(12) United States Patent
Smirman

(10) Patent No.: US 8,914,988 B2
(45) Date of Patent: *Dec. 23, 2014

(54) MEASUREMENT SYSTEM FOR VARUS/VALGUS ANGLES IN FEET

(71) Applicant: Marie Smirman, Rochester Hills, MI (US)

(72) Inventor: Marie Smirman, Rochester Hills, MI (US)

(*) Notice: Subject to any disclaimer, the term of this patent is extended or adjusted under 35 U.S.C. 154(b) by 0 days.

This patent is subject to a terminal disclaimer.

(21) Appl. No.: 13/920,279

(22) Filed: Jun. 18, 2013

(65) Prior Publication Data

US 2013/0276317 A1    Oct. 24, 2013

Related U.S. Application Data

(63) Continuation-in-part of application No. 13/249,570, filed on Sep. 30, 2011, now Pat. No. 8,479,405.

(60) Provisional application No. 61/388,096, filed on Sep. 30, 2010.

(51) Int. Cl.
*G01B 3/56* (2006.01)
*A61B 5/00* (2006.01)
*A61B 5/107* (2006.01)

(52) U.S. Cl.
CPC ............. *G01B 3/56* (2013.01); *A61B 5/6829* (2013.01); *A61B 5/0079* (2013.01); *A61B 5/1071* (2013.01)
USPC ............................................. 33/534; 33/515

(58) Field of Classification Search
CPC .... A61B 5/1072; A61B 5/107; A61B 5/1074; A61B 5/1078; A61B 5/1077; A43D 1/02; A43D 1/022; G01B 5/025; G01B 5/00; G01B 5/08

USPC ............. 33/534, 512, 515, 514.2, 1 BB
See application file for complete search history.

(56) References Cited

U.S. PATENT DOCUMENTS

| | | | | |
|---|---|---|---|---|
| 2,645,025 | A * | 7/1953 | Weinerman | 33/515 |
| 4,662,079 | A * | 5/1987 | Graf et al. | 33/512 |
| 6,625,897 | B2 * | 9/2003 | Tadin | 33/515 |
| 6,904,692 | B2 * | 6/2005 | Tadin | 33/515 |
| 7,125,509 | B1 * | 10/2006 | Smith | 33/515 |
| 7,343,691 | B2 * | 3/2008 | Long et al. | 33/555.4 |
| 7,516,560 | B2 * | 4/2009 | Long | 33/555.4 |
| 7,854,071 | B2 * | 12/2010 | Goonetilleke et al. | 33/515 |
| 7,938,788 | B2 * | 5/2011 | Shavelson | 33/515 |
| 7,975,390 | B2 * | 7/2011 | Goonetilleke et al. | 33/3 B |
| 8,479,405 | B2 * | 7/2013 | Smirman | 33/534 |
| 8,567,081 | B2 * | 10/2013 | Smith | 33/515 |

(Continued)

*Primary Examiner* — Yaritza Guadalupe-McCall
(74) *Attorney, Agent, or Firm* — Preston Smirman; Smirman IP Law, PLLC

(57) ABSTRACT

A measurement system is described for determining the varus and/or valgus angles of a pronating and/or supinating foot, especially when the subtalar joint of the foot is placed and/or maintained in a neutral position. When the user's foot is maintained in the subtalar joint neutral position, it causes a platform member to rotate relative to a correspondingly shaped depression formed in a base portion such that a top surface of the platform member is no longer in a substantially coplanar relationship with a top surface of the base portion. When this occurs, a bottom surface of the platform member is exposed. As a result, indicia are exposed which correspond to degree markings disposed on the bottom surface of the platform member. The degree markings indicate the angle that corresponds to the varus and/or valgus angles, and thus the amount of pronation and/or supination, of the user's foot.

20 Claims, 3 Drawing Sheets

(56) References Cited

U.S. PATENT DOCUMENTS

| | | | |
|---|---|---|---|
| 2005/0022407 A1* | 2/2005 | Tadin | 33/515 |
| 2006/0283243 A1* | 12/2006 | Peterson | 73/172 |
| 2009/0205213 A1* | 8/2009 | Goonetilleke et al. | 33/3 R |
| 2010/0229422 A1* | 9/2010 | Goonetilleke et al. | 33/515 |
| 2012/0079733 A1* | 4/2012 | Smirman | 33/534 |
| 2013/0276317 A1* | 10/2013 | Smirman | 33/515 |

* cited by examiner

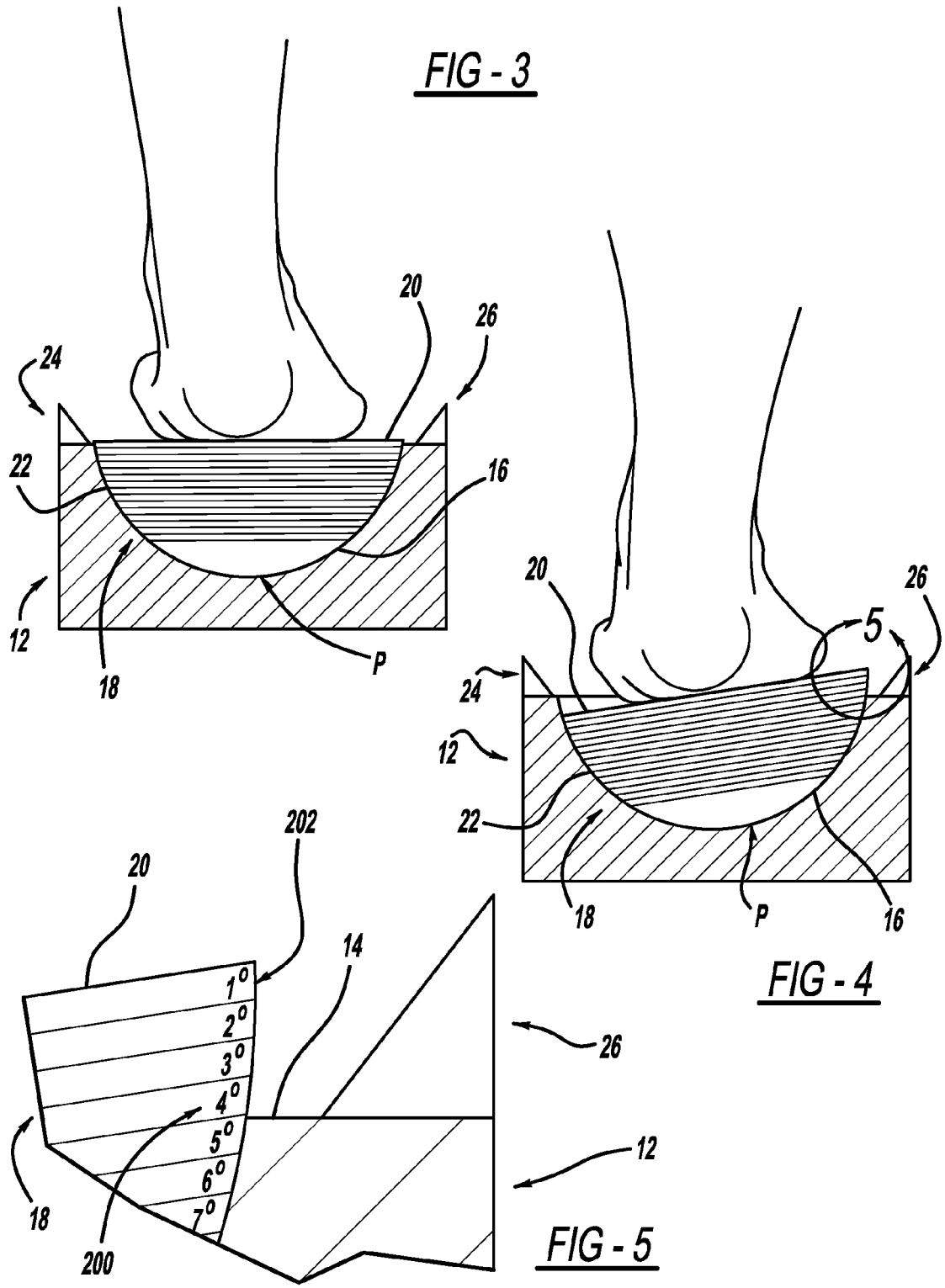

MEASUREMENT SYSTEM FOR VARUS/VALGUS ANGLES IN FEET

CROSS-REFERENCE TO RELATED APPLICATION

The instant application is a continuation-in-part of U.S. patent application Ser. No. 13/249,570, filed Sep. 30, 2011, pending, and claims priority to U.S. Provisional Patent Application Ser. No. 61/388,096, filed Sep. 30, 2010, the entire specifications of both of which are expressly incorporated herein by reference.

FIELD OF THE INVENTION

The present invention relates generally to measurement devices for feet and more specifically to a measurement system for determining the varus and/or valgus angles of a pronating and/or supinating foot, with respect to the knee joint axis, when the subtalar joint of the foot is placed and/or maintained in a neutral position.

BACKGROUND OF THE INVENTION

Conventional bicycles typically have pedals that are substantially perpendicular to the bike frame, that is, the pedals are parallel to the knee joint axis. However, many individuals have feet that are not parallel to the knee joint axis, especially when the feet are in the subtalar neutral position.

This situation is especially problematic for individuals with existing pronation and/or supination conditions, wherein significant rearfoot and/or forefoot valgus and/or varus conditions are present. For example, some of these individuals may have "bowed" lower legs (e.g., laterally or medially), and as a result, the supinators and/or the pronators attempt to compensate by maintaining a neutral or level foot posture relative to the bicycle pedal. In these situations, the bicyclist attempts to compensate for the valgus/varus conditions.

Because of these different mechanical conditions being present, the bicyclist's foot needs to maintain constant and consistent medial-lateral even pressure over the pedals, and without this even pressure, the muscles, bones, tendons and ligaments of the bicyclist's foot (as well as other parts of the body) can become stressed and/or injured as the ankle repeatedly rolls, or attempts to roll, either laterally or medially. In these situations, it is difficult for the rider to maintain proper contact and alignment between the soles of their shoes and the pedal surface. As a result, great effort must be made by these individuals to apply the requisite force necessary to propel the bicycle forward, thus making bicycle riding generally unenjoyable and competitive bicycle racing difficult, if not impossible.

A new and improved forefoot wedge for a piece of footwear, e.g., a shoe, such as, but not limited to exercise, therapeutic, or physiological footwear, is described in commonly-owned U.S. patent application Ser. No. 12/760,370, the entire specification of which is expressly incorporated herein by reference. The forefoot wedge can be formed of any formable or moldable material that is substantially firm, yet comfortable, when formed, molded, cured or dried. The formable or moldable material is used to uplift the forefoot area of the wearer's foot to cause the subtalar joint of the wearer to assume and/or maintain a neutral position. By way of a non-limiting example, the vertical leg/foot arrangement is being "shimmed level" to the shoe bottom medially/laterally (as the case may require) in the neutral position (e.g., subtalar neutral) in order to achieve relatively good alignment for the body, e.g., when riding a bicycle.

Conventionally, in order to determine what the overall wedge height or thickness of the forefoot wedge should be, it was first necessary to determine the forefoot varus/valgus angle and the rearfoot varus/valgus angle, and then combine the two angles to geometrically determine the overall wedge height or thickness. With respect to pronators, the respective forefoot/rearfoot measurements will yield two different varus angles; however, it should be appreciated that one of the measurements might yield either a 0 degree angle or a very slight valgus angle (e.g., typically in the rearfoot angle measurement). However, pronators typically yield an overall or total positive varus angle result. With respect to supinators, the respective forefoot/rearfoot measurements will yield two different valgus angles; however, it should be appreciated that one of the measurements might yield either a 0 degree angle or a very slight varus angle (e.g., typically in the rearfoot angle measurement). However, supinators typically yield an overall or total negative valgus angle result.

One method to determine the forefoot valgus angle for a supinator (or suspected supinator), required that the wearer's foot be held in non-weight bearing subtalar neutral position (e.g., by a podiatrist), or as close thereto as possible. An appropriate diagnostic tool, such as but not limited to a goniometer was used to measure the valgus angle formed by the tilt of the bottom of the forefoot relative to the bottom of the heel portion. If the wearer's other foot is also affected, a similar measurement would be done for the other foot.

One method to determine the forefoot varus angle for a pronator (or suspected pronator) required that the wearer's foot be held in non-weight bearing subtalar neutral position (e.g., by a podiatrist), or as close thereto as possible. An appropriate diagnostic tool, such as but not limited to a goniometer was used to measure the varus angle formed by the tilt of the bottom of the forefoot relative to the bottom of the heel portion. If the wearer's other foot is also affected, a similar measurement would be done for the other foot.

One method to determine the rearfoot valgus angle for a supinator (or suspected supinator) required that the wearer's foot be held in non-weight bearing subtalar neutral position (e.g., by a podiatrist) or as close thereto as possible. An appropriate diagnostic tool, such as but not limited to a goniometer was used to measure the valgus angle formed by the intersection of the vertical axis extending downwardly through the lower leg area and the vertical axis extending upwardly through the middle of the heel portion. The intersection of these two axes forms a vertex of the rearfoot valgus angle.

One method to determine the rearfoot varus angle for a pronator (or suspected pronator) required that the wearer's foot be held in non-weight bearing subtalar neutral position (e.g., by a podiatrist), or as close thereto as possible. An appropriate diagnostic tool, such as but not limited to a goniometer was used to measure the varus angle formed by the intersection of the vertical axis extending downwardly through the lower leg area and the vertical axis extending upwardly through the middle of the heel portion. The intersection of these two axes forms a vertex of the rearfoot varus angle.

However, all of these conventional measurements are typically made with reference to the bottom third of the tibia.

One method to determine the total wedge angle, and thus the overall wedge height or thickness of the forefoot wedge, includes combining the forefoot angle (whether it be varus or valgus in nature) with the rearfoot angle (whether it be varus or valgus in nature) according to the following formula: Total Wedge Angle=Forefoot Angle (+varus or −valgus)+Rearfoot Angle (+varus or −valgus).

However, the above-described methodology is rather cumbersome and typically requires the user or, more likely, an assistant such as a podiatrist, to be able to accurately use a goniometer to precisely determine the various varus/valgus angles while simultaneously trying to maintain the wearer's foot in non-weight bearing subtalar neutral position. Accordingly, it would not be unexpected to see significant measurement errors and resulting under-correction or over-correction of the pronation/supination conditions with wedge heights that are either too low or too high.

Therefore, it would be advantageous to provide a new and improved measurement tool for determining the varus and/or valgus angles of a pronating and/or supinating foot when the subtalar joint of the foot is placed and/or maintained in a neutral position.

SUMMARY OF THE INVENTION

In accordance with the general teachings of the present invention, a new and improved measurement system is provided for determining the varus and/or valgus angles of a pronating and/or supinating foot, especially when the subtalar joint of the foot is placed and/or maintained in a neutral position. More specifically, the present invention provides a system and method to measure the varus/valgus angles with reference to the knee joint axis, as it is believed to be desired for proper bicycling technique and other non-weight bearing activities. This measurement system and method may therefore result in larger (although more accurate) varus/valgus angles than conventional measurement techniques.

In accordance with one embodiment of the present invention, a system for determining the varus and/or valgus angles of a pronating and/or supinating foot is provided, comprising:
    a base portion having a top surface;
    an area defining a depression formed in the top surface; and
    a platform member having a substantially planar top surface and a bottom surface, wherein the bottom surface is selectively operable to be received in and rotatable about the depression such that the top surface of the platform member is selectively operable to achieve and/or maintain a substantially coplanar orientation with respect to the top surface of the base portion.

In accordance with one aspect of this embodiment, at least one mirror member is provided on the top surface of the base portion.

In accordance with one aspect of this embodiment, a support system is provided, wherein the support system comprises: a support member that allows a user to place their leg over the support member such that their foot can rest on the top surface of the platform member.

In accordance with one aspect of this embodiment, the support member is selectively operable to maintain the user's knee/upper leg joint axis horizontal or parallel to the top surface of the platform member.

In accordance with one aspect of this embodiment, at least one adjustment system is provided to adjust the relative height of the support member.

In accordance with one aspect of this embodiment, at least one seat member is provided that is selectively operable to permit the user to sit thereon.

In accordance with one aspect of this embodiment, when a user's foot rests on the top surface of the platform member such that the user's foot maintains the top surface of the platform member in a substantially coplanar relationship with the top surface of the base portion, the user's foot is in an uncorrected supinating and/or pronating position.

In accordance with one aspect of this embodiment, the user's foot is selectively operable to be manipulated such that the user's foot maintains a subtalar joint neutral position.

In accordance with one aspect of this embodiment, when the user's foot is maintained in the subtalar joint neutral position, the platform member rotates relative to the depression such that top surface of the platform member is no longer in a substantially coplanar relationship with the top surface of the base portion.

In accordance with one aspect of this embodiment, when the platform member rotates relative to the depression such that top surface of the platform member is no longer in a substantially coplanar relationship with the top surface of the base portion, the bottom surface of the platform member is exposed.

In accordance with one aspect of this embodiment, the bottom surface of the platform member has indicia formed thereon.

In accordance with one aspect of this embodiment, the indicia substantially correspond to degree markings.

In accordance with one aspect of this embodiment, the degree markings substantially correspond to a varus and/or valgus angle of the user's foot.

In accordance with one aspect of this embodiment, the degree markings substantially correspond to a varus and/or valgus angle of the user's foot when the user's foot maintains a subtalar joint neutral position.

In accordance with one aspect of this embodiment, the degree markings extend up to 90 degrees along an arc line of the bottom surface of the platform member.

In accordance with an alternative embodiment of the present invention, a system for determining the varus and/or valgus angles of a pronating and/or supinating foot is provided, comprising:
    a base portion having a top surface;
    an area defining a depression formed in the top surface; and
    a platform member having a substantially planar top surface and a bottom surface, wherein the bottom surface is selectively operable to be received in and rotatable about the depression such that the top surface of the platform member is selectively operable to achieve and/or maintain a substantially coplanar orientation with respect to the top surface of the base portion;
    wherein when a user's foot rests on the top surface of the platform member such that the user's foot maintains the top surface of the platform member in a substantially coplanar relationship with the top surface of the base portion, the user's foot is in an uncorrected supinating and/or pronating position.

In accordance with one aspect of this embodiment, the user's foot is selectively operable to be manipulated such that the user's foot maintains a subtalar joint neutral position, wherein when the user's foot is maintained in the subtalar joint neutral position, the platform member rotates relative to the depression such that top surface of the platform member is no longer in a substantially coplanar relationship with the top surface of the base portion.

In accordance with one aspect of this embodiment, when the platform member rotates relative to the depression such that top surface of the platform member is no longer in a substantially coplanar relationship with the top surface of the base portion, the bottom surface of the platform member is exposed, wherein the bottom surface of the platform member has indicia formed thereon.

In accordance with one aspect of this embodiment, the indicia substantially correspond to degree markings, wherein the degree markings substantially correspond to a varus and/or valgus angle of the user's foot when the user's foot maintains a subtalar joint neutral position.

In accordance with one aspect of this embodiment, the degree markings extend up to 90 degrees along an arc line of the bottom surface of the platform member.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

Other advantages of the present invention will be readily appreciated as the same becomes better understood by reference to the following detailed description when considered in connection with the accompanying drawings wherein:

FIG. 3 is a schematic view of a supinating right foot placed on a measurement system, in accordance with a third embodiment of the present invention;

FIG. 4 is a schematic view of the supinating right foot maintained in a neutral subtalar joint position on a measurement system, in accordance with a fourth embodiment of the present invention;

FIG. 5 is a detail view of an angle indication system of a measurement system, in accordance with a fifth embodiment of the present invention;

The same reference numerals refer to the same parts throughout the various Figures.

DETAILED DESCRIPTION OF THE INVENTION

The following description of the preferred embodiment(s) is merely exemplary in nature and is in no way intended to limit the invention, or uses.

Figure 1:
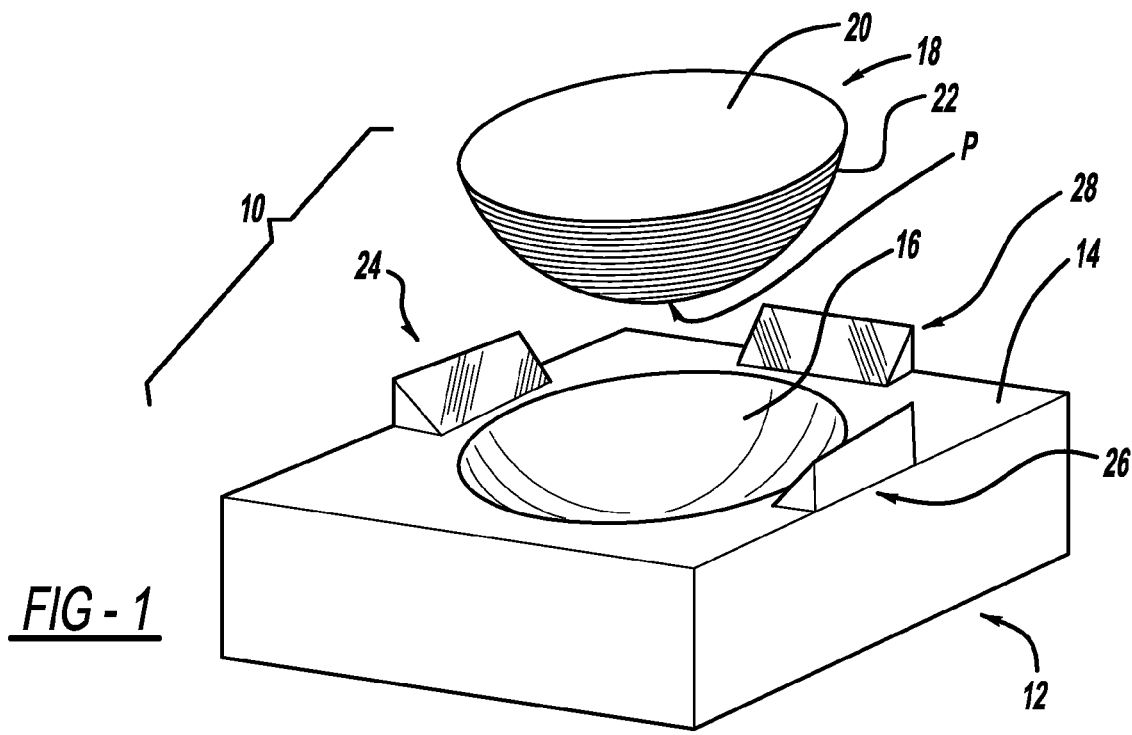
FIG. 1 is an exploded view of a measurement system, in accordance with one embodiment of the present invention.

Referring to FIG. 1, there is shown a measurement system generally at 10 that is selectively operable to determine the varus and/or valgus angles of a pronating and/or supinating foot, especially when the subtalar joint of the foot is placed and/or maintained in a neutral position. The system 10 primarily includes a base portion 12 that can be configured in any number of shapes including, but not limited to squares, rectangles, circles, ovals, and/or the like. On a top surface 14 of the base portion 10 there is provided an area defining a depression 16 formed therein. In this view, the depression 16 is substantially hemispherically shaped. It should be appreciated that other shapes, other than a hemisphere, may be used in the practice of the present invention. A platform member 18, which includes a substantially planar top surface 20 and a substantially hemispherically shaped bottom surface 22 is intended to interoperate with the depression 16. It should be appreciated that other shapes, other than a hemisphere, may be used in the practice of the present invention. By way of a non-limiting example, the bottom surface 22 is intended to be received in the depression 16 such that the top surface 20 is substantially coplanar with the top surface 14. Additionally, it is intended that the bottom surface 22 moves easily relative to the depression 16 so as to freely rotate thereabout, and especially has freedom of movement in any direction. By way of a non-limiting example, the bottom surface 22 and/or the depression 16 can be coated with a lubricant or can be comprised of a material with a low coefficient of friction so as to provide a very smooth and/or slick surface.

On one or more surfaces of the top surface 14, there is provided a mirror member 24, and more preferably, two mirror members 24, 26, respectively, that are provided in proximity to the depression 16, the intended purpose of which will be described herein. Additionally, another mirror member 28 can be provided along a rear portion of the top surface 14, the intended purpose of which will be described herein.

Figure 2:
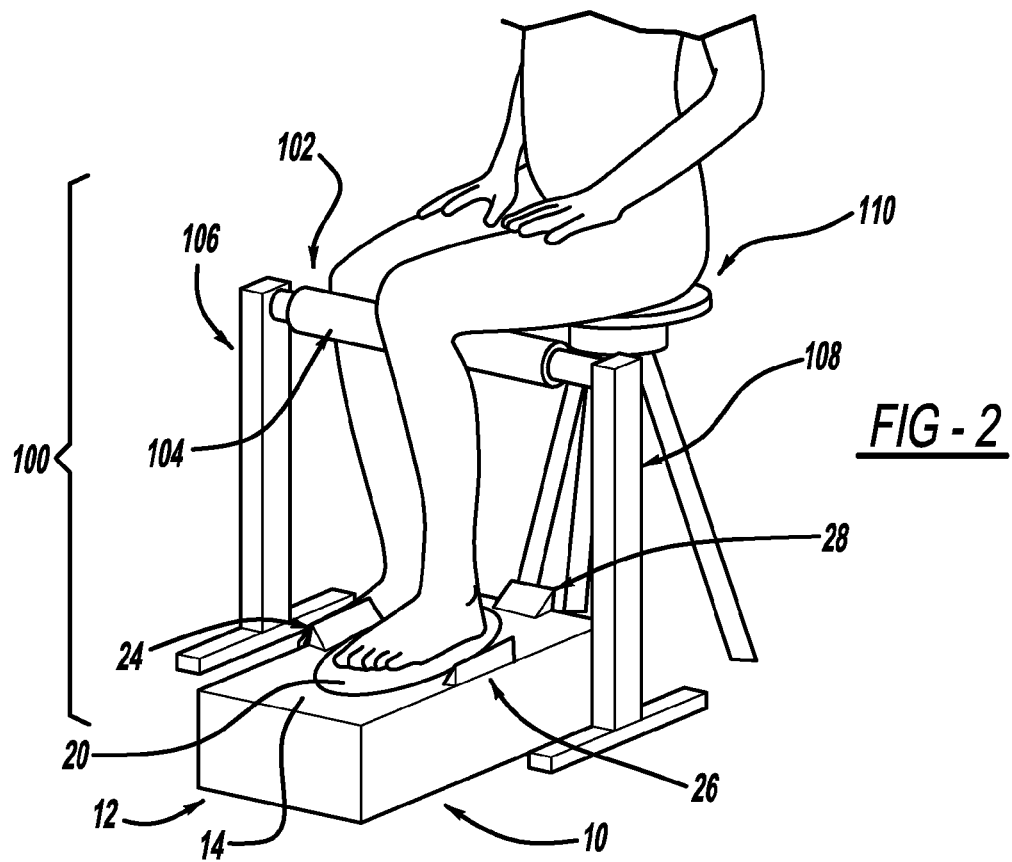
FIG. 2 is a schematic view of a person using an alternative measurement system, in accordance with a second embodiment of the present invention.

Referring to FIG. 2, there is shown an alternative measurement system generally at 100 that is also selectively operable to determine the varus and/or valgus angles of a pronating and/or supinating foot, especially when the subtalar joint of the foot is placed and/or maintained in a neutral position. System 100 includes the measurement system 10, as previously described above. However, system 100 also can include a support system 102 that includes a support member 104 that allows a user to place their respective leg over the support member 104 such that their respective foot can rest on the top surface 20 of the platform member 18.

The support member 104 is intended to aid in maintaining the user's knee/upper leg joint axis horizontal or parallel to the top surface 20 of the platform member 18 and provide stability during the measuring process and serving as a reference point for measuring the aforementioned varus and/or valgus angles.

To adjust the relative height of the support member 104, one or more adjustment systems 106, 108, respectively, (e.g., a "telescoping" tube within a tube system and/or the like) can be provided to raise or lower the height of the support member 104, e.g. to accommodate the variability of individual leg lengths. Additionally, a seat member 110 can be provided to allow the user to sit down when the measurement process is conducted. The seat member 110 can also include the capability to be raised or lowered as needed, e.g. to accommodate the variability of individual leg lengths.

In any event, it is preferred that the user's respective foot initially rests on the top surface 20 of the platform member 18 such that the foot maintains the top surface 20 of the platform member 18 in a coplanar or substantially coplanar relationship with the top surface 14 of the base portion 12. That is, the foot is in the uncorrected position, i.e., either supinating or pronating.

In order to determine the varus and/or valgus angles of a pronating and/or supinating foot, especially when the subtalar joint of the foot is placed and/or maintained in a neutral position, reference is made to FIGS. 3-7 (note that mirror member 28 has been removed for purposes of illustration).

Referring to FIG. 3, the rear of a user's right supinating foot is shown resting upon the top surface 20 of the platform member 18 such that the foot maintains the top surface 20 of the platform member 18 in a coplanar or substantially coplanar relationship with the top surface 14 of the base portion 12. That is, the foot is in the uncorrected position, i.e., supinating in this case.

Referring to FIGS. 4 and 5, and in accordance with an illustrative example, the user, or an assistant, rotates or otherwise manipulates the user's foot such that the direction of the foot's heel substantially aligns with the lower leg area.

That is, the user, or an assistant, rotates or otherwise manipulates the user's foot to maintain a subtalar joint neutral position. If the user does not have an assistant available, he or she can determine if their heel substantially aligns with their lower leg area by looking at the reflection in mirror member 28.

When the user's foot is maintained in the subtalar joint neutral position, it causes the platform member 18 to rotate relative to the depression 16 such that top surface 20 of the platform member 18 is no longer in a coplanar or substantially coplanar relationship with the top surface 14 of the base portion 12. When this occurs, the bottom surface 22 of the platform member 18 is exposed. By way of a non-limiting example, indicia 200 are exposed which correspond to degree markings 202 disposed on the bottom surface 22 of the platform member 18. The degree markings 202 indicate the angle that corresponds to the varus and/or valgus angles and thus the amount of supination of the foot. In this view, the degree markings 202 indicate that the varus and/or valgus angle is equivalent to 4 degrees of supination of this particular foot (it should be appreciated that the degree of the varus and/or valgus angle (and thus the corresponding amount of supination) can be either less than or greater than this number of degrees and is shown here for illustrative purposes only). The degree markings 202 can extend, for example, up to or around 90 degrees along any particular arc line of the bottom surface 22 of the platform member 18 and terminate at the pole P of the platform member 18 (it should be noted that all of the 90 degree markings have not been depicted for purposes of clarity). Further, it should be appreciated that it may not be necessary to delineate all of the 90 degree markings on the bottom surface 22, as most individuals do not have a supination/pronation condition that is so severe that they would cause the platform member 18 to rotate the platform member 18 such that all of the 90 degree markings are exposed. By way of a non-limiting example, only forty-five (45) degree markings on the bottom surface 22 may be adequate for assessing most supinating/pronating individuals. By way of another non-limiting example, only thirty (30) degree markings on the bottom surface 22 may also be adequate for assessing most supinating/pronating individuals. To facilitate the viewing of the degree markings 202, the mirror members 24, 26, 28, respectively, can be used by the user or the assistant to accurately "read" the degree markings 202. In this manner, the foot can be held in the subtalar joint neutral position, without the user or the assistant having to use a conventional device, such as a goniometer, and risk having the foot come out of the subtalar joint neutral position, thus compromising the accuracy of the angle measurement.

Figure 6:
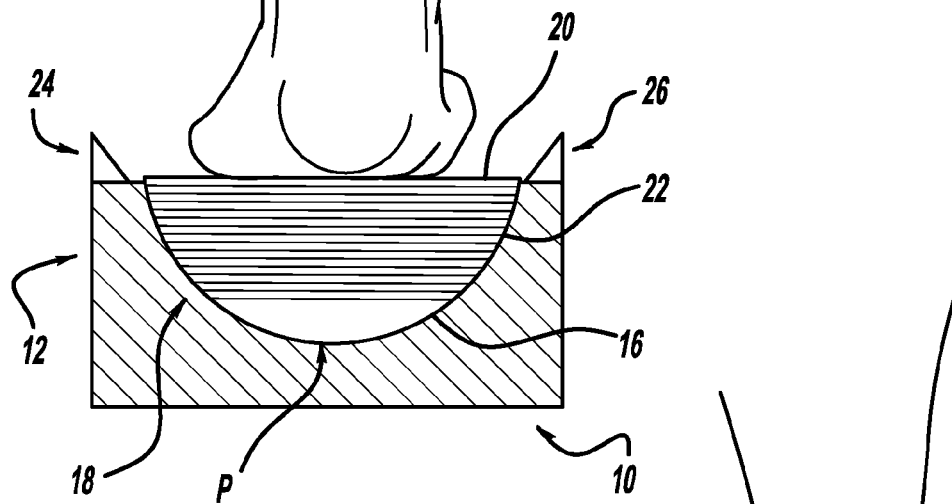
FIG. 6 is a schematic view of a pronating left foot placed on a measurement system, in accordance with a sixth embodiment of the present invention.
Figure 7:
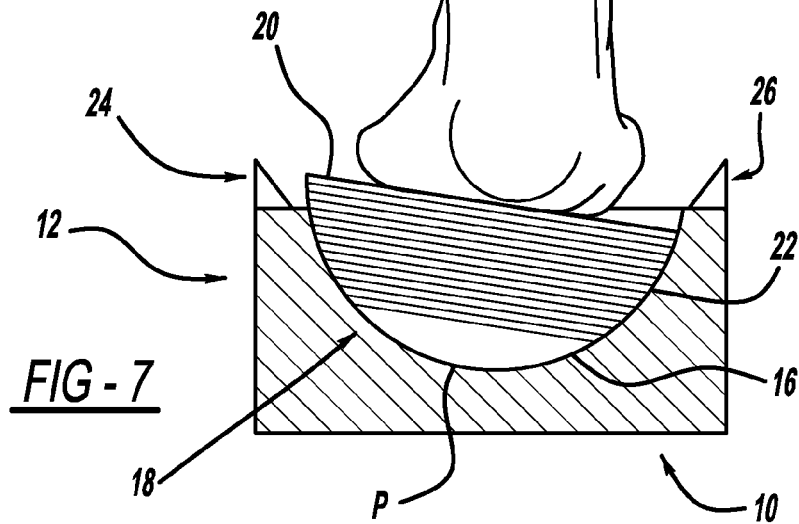
FIG. 7 is a schematic view of the pronating left foot maintained in a neutral subtalar joint position on a measurement system, in accordance with a seventh embodiment of the present invention.

Referring to FIGS. 6 and 7, the rear of a user's left pronating foot is shown resting upon the top surface 20 of the platform member 18 such that the foot maintains the top surface 20 of the platform member 18 in a coplanar or substantially coplanar relationship with the top surface 14 of the base portion 12. That is, the foot is in the uncorrected position, i.e., pronating in this case.

As with the process described in connection with FIGS. 4 and 5, the user, or an assistant, rotates or otherwise manipulates the user's foot such that the direction of the foot's heel substantially aligns with the lower leg area. That is, the user, or an assistant, rotates or otherwise manipulates the user's foot to maintain a subtalar joint neutral position. Again, if the user does not have an assistant available, he or she can determine if their heel substantially aligns with their lower leg area by looking at the reflection in mirror member 28.

When the user's foot is maintained in the subtalar joint neutral position, it causes the platform member 18 to rotate relative to the depression 16 such that top surface 20 of the platform member 18 is no longer in a coplanar or substantially coplanar relationship with the top surface 14 of the base portion 12. When this occurs, the bottom surface 22 of the platform member 18 is exposed. As with the description of the process in connection with FIG. 5, indicia 200 are exposed which correspond to degree markings 202 disposed on the bottom surface 22 of the platform member 18. The degree markings 202 indicate the varus and/or valgus angle that corresponds to the amount of pronation of the foot. Again, to facilitate the viewing of the degree markings 202, the mirror members 24, 26, 28, respectively, can be used by the user or the assistant to accurately "read" the degree markings 202. In this manner, the foot can be held in the subtalar joint neutral position, without the user or the assistant having to use a conventional device, such as a goniometer, and risk having the foot come out of the subtalar joint neutral position, thus compromising the accuracy of the angle measurement.

The measurements of the degrees of the varus and/or valgus angles, and thus the amount of supination/pronation, can allow the user to have a wedge to be constructed that has the proper angle profile to eliminate, or at least lessen, the amount of supination/pronation of that particular foot.

This measurement system may be used to determine the wedge angle that may properly align feet for bicycling purposes, use of gym equipment such as leg presses, and use of other exercise and/or sports equipment that puts the feet/legs in a non-weight bearing position. By way of a non-limiting example, the wedge constructed in accordance with the system and/or method of the present invention may be placed onto the bottom of the user's foot or shoe, as opposed to being placed inside the user's shoe, as is typically done with conventional orthotics.

While the invention has been described with reference to an exemplary embodiment, it will be understood by those skilled in the art that various changes can be made and equivalents can be substituted for elements thereof without departing from the scope of the invention. In addition, many modifications can be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A system for determining the varus and/or valgus angles of a pronating and/or supinating foot, comprising:
    a base portion having a top surface;
    an area defining a depression formed in the top surface; and
    a platform member having a substantially planar top surface and a bottom surface, wherein the bottom surface is selectively operable to be received in and freely rotatable in any direction about the depression such that the top surface of the platform member is selectively operable to achieve and/or maintain a substantially coplanar orientation with respect to the top surface of the base portion.

2. The determining system according to claim 1, further comprising at least one mirror member provided on the top surface of the base portion.

3. The determining system according to claim 1, further comprising a support system, wherein the support system comprises:
    a support member that allows a user to place their leg over the support member such that their foot can rest on the top surface of the platform member.

4. The determining system according to claim 3, wherein the support member is selectively operable to maintain the user's knee/upper leg joint axis horizontal or parallel to the top surface of the platform member.

5. The determining system according to claim 3, further comprising at least one adjustment system to adjust the relative height of the support member.

6. The determining system according to claim 3, further comprising at least one seat member that is selectively operable to permit the user to sit thereon.

7. The determining system according to claim 1, wherein when a user's foot rests on the top surface of the platform member such that the user's foot maintains the top surface of the platform member in a substantially coplanar relationship with the top surface of the base portion, the user's foot is in an uncorrected supinating and/or pronating position.

8. The determining system according to claim 7, wherein the user's foot is selectively operable to be manipulated such that the user's foot maintains a subtalar joint neutral position.

9. The determining system according to claim 8, wherein when the user's foot is maintained in the subtalar joint neutral position, the platform member rotates relative to the depression such that top surface of the platform member is no longer in a substantially coplanar relationship with the top surface of the base portion.

10. The determining system according to claim 9, wherein when the platform member rotates relative to the depression such that top surface of the platform member is no longer in a substantially coplanar relationship with the top surface of the base portion, the bottom surface of the platform member is exposed.

11. The determining system according to claim 1, wherein the bottom surface of the platform member has indicia formed thereon.

12. The determining system according to claim 11, wherein the indicia substantially correspond to degree markings.

13. The determining system according to claim 12, wherein the degree markings substantially correspond to a varus and/or valgus angle of the user's foot.

14. The determining system according to claim 12, wherein the degree markings substantially correspond to a varus and/or valgus angle of the user's foot when the user's foot maintains a subtalar joint neutral position.

15. The determining system according to claim 12, wherein the degree markings extend up to 90 degrees along an arc line of the bottom surface of the platform member.

16. A system for determining the varus and/or valgus angles of a pronating and/or supinating foot, comprising:
 a base portion having a top surface;
 an area defining a depression formed in the top surface; and
 a platform member having a substantially planar top surface and a bottom surface, wherein the bottom surface is selectively operable to be received in and freely rotatable in any direction about the depression such that the top surface of the platform member is selectively operable to achieve and/or maintain a substantially coplanar orientation with respect to the top surface of the base portion;
 wherein when a user's foot rests on the top surface of the platform member such that the user's foot maintains the top surface of the platform member in a substantially coplanar relationship with the top surface of the base portion, the user's foot is in an uncorrected supinating and/or pronating position.

17. The determining system according to claim 16, wherein the user's foot is selectively operable to be manipulated such that the user's foot maintains a subtalar joint neutral position, wherein when the user's foot is maintained in the subtalar joint neutral position, the platform member rotates relative to the depression such that top surface of the platform member is no longer in a substantially coplanar relationship with the top surface of the base portion.

18. The determining system according to claim 17, wherein when the platform member rotates relative to the depression such that top surface of the platform member is no longer in a substantially coplanar relationship with the top surface of the base portion, the bottom surface of the platform member is exposed, wherein the bottom surface of the platform member has indicia formed thereon.

19. The determining system according to claim 18, wherein the indicia substantially correspond to degree markings, wherein the degree markings substantially correspond to a varus and/or valgus angle of the user's foot when the user's foot maintains a subtalar joint neutral position.

20. The determining system according to claim 19, wherein the degree markings extend up to 90 degrees along an arc line of the bottom surface of the platform member.

\* \* \* \* \*